United States Patent [19]

Johnson et al.

[11] 4,338,325

[45] Jul. 6, 1982

[54] PGI$_2$ PHARMACOLOGICALLY ACCEPTABLE SALTS

[75] Inventors: Roy A. Johnson, Kalamazoo; Frank H. Lincoln, Portage; John E. Pike, Kalamazoo, all of Mich.

[73] Assignee: The Upjohn Company, Kalamazoo, Mich.

[21] Appl. No.: 200,690

[22] Filed: Oct. 27, 1980

Related U.S. Application Data

[63] Continuation-in-part of Ser. No. 819,940, Jul. 28, 1977, which is a continuation-in-part of Ser. No. 725,550, Sep. 22, 1976, abandoned, which is a continuation-in-part of Ser. No. 716,770, Aug. 23, 1976, abandoned.

[51] Int. Cl.$^3$ ............... A61K 31/557; C07D 307/935
[52] U.S. Cl. ...................................... 424/285; 549/465
[58] Field of Search ...................... 260/346.22, 346.73; 542/421; 424/285

[56] References Cited

U.S. PATENT DOCUMENTS 3,598,858  8/1971  Bergstrom et al. ................. 562/503

OTHER PUBLICATIONS

Moncada et al., Prostaglandins, vol. 12, pp. 658–713, (1976).

*Primary Examiner*—Henry R. Jiles
*Assistant Examiner*—Bernard Dentz
*Attorney, Agent, or Firm*—Robert A. Armitage

[57] ABSTRACT

The present invention relates to PGI$_2$ pharmacologically acceptable salts, having pharmacological activity. Particularly, the compounds described herein are useful as platelet aggregation inhibitors.

6 Claims, No Drawings

PGI₂ PHARMACOLOGICALLY ACCEPTABLE SALTS

DESCRIPTION

CROSS REFERENCE TO RELATED APPLICATIONS

This application is a continuation-in-part of co-pending application Ser. No. 819,940, filed July 28, 1977; which is a continuation-in-part of Ser. No. 725,550, filed Sept. 22, 1976, now abandoned; which was a continuation-in-part of Ser. No. 716,770, filed Aug. 23, 1976, now abandoned.

BACKGROUND OF THE INVENTION

The present invention relates to novel compositions of matter which are derivatives of prostacyclin or PGI₂. The chemical name for prostacyclin is (5Z)-5,6-didehydro-9-deoxy-6,9α-epoxy-PGF₁α. Specifically the present invention relates to PGI₂ pharmacologically acceptable salts.

Prostacyclin itself was first reported as "PGX" by Moncada and his co-workers. See Moncada, et al., Prostaglandins 12:658–713 (1976). Prostacyclin is a circulating hormone in the arterial circulation of mammals. See "Prostacyclin As A Circulating Hormone", Nature 273:767–768 (June 29, 1978) and Grycleweski, R. J., et al., "Generation of Prostacyclin By Lungs In Vivo And Its Release Into Arterial Circulation," Nature 273:765–767 (June 29, 1978).

PRIOR ART

Subsequent to any invention described herein the existence of prostacyclin as a naturally-occurring composition of matter was reported in the aforementioned references.

SUMMARY OF THE INVENTION

The present invention relates to
a composition of matter consisting essentially of a pharmacologically acceptable salt of a compound of formula I

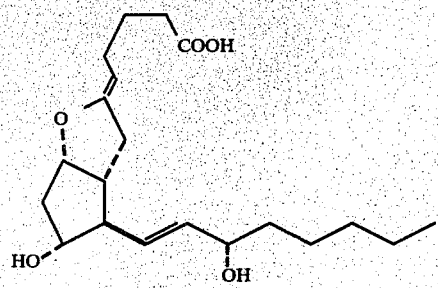

and
a parenteral pharmaceutical composition characterized in being prepared from
(1) a free flowing powder form of the sodium salt of PGI₂, a compound of formula I

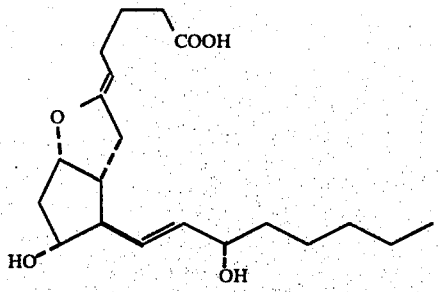

and
(2) a conventional pharmaceutical diluent for parenteral formulations.

Compounds in accordance with the present invention are prepared by chemical methods and have pharmacological uses. Accordingly, compounds in accordance with the present invention are useful for a variety of pharmacological purposes. Accordingly, the compounds in accordance with the present invention are especially useful whenever it is desired to inhibit platelet aggregation, to reduce the adhesive character of platelets, and to remove or prevent the formation of thrombi in mammals, including man. For example, these compounds are useful in the treatment and prevention of myocardial infarcts, to treat and prevent post-operative thrombosis, to promote patency of vascular drafts following surgery, and to treat conditions such as atherosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long-term prophylaxis following myocardial infarcts and strokes. For these purposes, the compounds are administered systemically, e.g., intravenously, subcutaneously, intramuscularly, and in the form of sterile implants for prolonged action. For rapid response, especially in emergency situations, the intravenous route of administration is preferred. Dosages in the range about 0.01 to about 10 mg/kg of body weight per day are used, the exact dose depending on the age, weight, and condition of the patient or animal, and on the frequency and route of administration.

The addition of these compounds to whole blood provides in vitro applications, such as storage of whole blood to be used in heart-lung machines. Additionally, whole blood containing these compounds can be circulated through limbs and organs, e.g., heart and kidneys, whether attached to the original body, detached and being preserved or prepared for transplant, or attached to a new body. Blocking of aggregated platelets is avoided by the presence of these compounds. For this purpose, the compound is added gradually or in single or multiple portions to the circulating blood, to the blood of the donor person or animal, to the perfused whole body, attached or detached, to the recipient, or to two or all of those at a total steady state dose of about 0.001–1.0 μg/ml of whole blood. These compounds are also useful in preparing platelet-rich concentrates from blood for use in treating thrombocytopenia or in chemotherapy.

DESCRIPTION OF THE PREFERRED EMBODIMENTS

The present invention especially provides for the preparation of compositions of matter consisting essentially of pharmacologically acceptable salts of prostacyclin. Most conveniently, these pharmacologically acceptable salts of prostacyclin are prepared from the corresponding methyl ester, $PGI_2$ methyl ester or (5Z)-9-deoxy-6,9α-epoxy-5,6-didehydro-$PGF_1$, methyl ester. The preparation of the methyl ester starting material is described in U.S. Pat. No. 4,158,667, incorporated here by reference (e.g., Example 7 therein). From the crystalline form of this methyl ester described in U.S. Pat. No. 4,158,667, compositions of matter consisting essentially of pharmacologically acceptable salts of prostacyclin are prepared in accordance with the following examples:

EXAMPLE 1

(5Z)-9-Deoxy-6,9α-epoxy-$\Delta^5$-$PGF_1$, sodium salt.

A mixture of 0.030 g (5Z)-9-deoxy-6,9α-epoxy-$\Delta^5$-$PGF_1$, methyl ester in 5 ml of methanol is treated with 9 ml of 0.01 N NaOH and stirred at about 250° C. for 72 hr. The solution is then concentrated, diluted with 5 ml of water, frozen at about $-75°$ C. and lyophilized overnight. The title compound is obtained as a white free-flowing powder having infrared absorption at 3320, 1693, 1555, and 1470 cm$^{-1}$.

The procedure above is repeated using larger quantities. From 0.150 g of the enol ether methyl ester there is obtained 0.155 g of the title compound as a white free-flowing powder. A sample of the material dissolved in methanol-water shows practically no mobility by TLC on silica gel plates in acetone-dichloromethane (3:7), compared with the starting material which has $R_f$ 0.45 (TLC on silica gel in acetone-dichloromethane (3:7) using plates pretreated in triethylamine-(5%)-dichloromethane).

Following the procedure of Example 1, but replacing sodium hydroxide with excess sodium carbonate suspended in water, there is obtained the title compound after 72 hr at about 25° C. The product is precipitated with acetonitrile.

EXAMPLE 2

(5Z)-9-Deoxy-6,9α-epoxy-$\Delta^5$-$PGF_1$, benzyltrimethylammonium salt.

A solution of 0.25 g of (5Z)-9-deoxy-6,9α-epoxy-$\Delta^5$-$PGF_1$, methyl ester in 5 ml of methanol is treated with one ml of water and 0.5 ml of methanolic solution (40%) of benzyltrimethylammonium hydroxide. The mixture is left standing at about 25° C. for 22 hr and then concentrated to one-fourth volume. The concentrate is made up with water to a volume of 25 ml, frozen with Dry Ice and lyophilized to yield the title compound, a solid, having infrared absorption at 3375, 1700, 1570, 1395, 1125, 1090, 1035, 975, 895, 780, 725, and 705 cm$^{-1}$.

EXAMPLE 3

(5Z)-9-Deoxy-6,9α-epoxy-$\Delta^5$-$PGF_1$, tetramethylammonium salt

A solution of 0.25 g of (5Z)-9-Deoxy-6,9α-epoxy-$\Delta^5$-$PGF_1$, methyl ester in 5 ml of methanol is treated with one ml of an aqueous solution (10%) of tetramethylammonium hydroxide, thereafter following the procedure of Example 2, to obtain the title compound, a solid, having infrared absorption at 3375, 1695, 1570, 1495, 1395, 1125, 1090, 1035, 970, and 955 cm$^{-1}$.

Accordingly, there is provided by the present invention novel compositions of matter consisting essentially of a single, pharmacologically acceptable salt of prostacyclin.

Accordingly, the present compositions of matter consisting essentially of a pharmacologically acceptable salt of prostacyclin are surprisingly and unexpectedly more useful than preparations of prostacyclin heretofore obtainable from biological sources in that the novel compositions of matter are (1) highly chemically homogeneous (2) more readily sterilized for parenteral administration, (3) more conveniently and elegantly formulated as pharmaceutical entities, and (4) more efficacious in obtaining prostaglandin-like biological effects.

Thus, the present invention provides compositions of matter surprisingly and unexpectedly more useful than forms of prostacyclin known prior to the present invention.

We claim:

1. A composition of matter consisting essentially of a pharmacologically acceptable salt of a compound of formula I

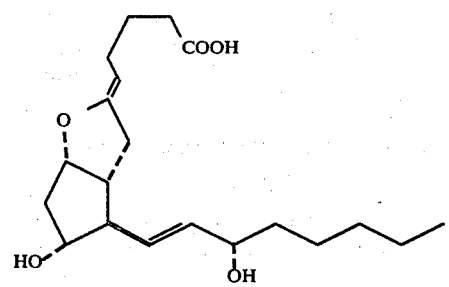

2. A composition according to claim 1 wherein said pharmacologically acceptable salt is the benzyltrimethylammonium salt.

3. A composition according to claim 1 wherein said pharmacologically acceptable salt is the tetramethylammonium salt.

4. A composition according to claim 1 wherein said pharmacologically acceptable salt is the sodium salt.

5. A composition according to claim 4 in a free flowing powder form.

6. A parenteral pharmaceutical composition for inhibition of platelet aggregation characterized in being prepared from (1) a free flowing powder form of the sodium salt of $PGI_2$, a compound of formula I

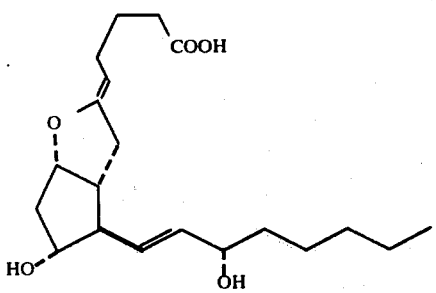
and
(2) a conventional pharmaceutical diluent for parenteral formulations, such that the sodium salt of PGI$_2$ is present in said composition at a concentration sufficient to inhibit platelet aggregation upon administration of a said composition in a predetermined volume or at a predetermined rate.
* * * * *